(12) United States Patent
Berberich et al.

(10) Patent No.: US 8,814,886 B2
(45) Date of Patent: Aug. 26, 2014

(54) THREAD CATCHER FOR SURGICAL SEWING MATERIAL

(75) Inventors: Sascha Berberich, Tuttlingen (DE); Martin Oberlaender, Engen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 545 days.

(21) Appl. No.: 12/398,244

(22) Filed: Mar. 5, 2009

(65) Prior Publication Data
US 2010/0057111 A1    Mar. 4, 2010

(30) Foreign Application Priority Data
Sep. 4, 2008  (DE) .................... 20 2008 011 769 U

(51) Int. Cl.
 *A61B 17/04* (2006.01)
 *A61B 17/22* (2006.01)
(52) U.S. Cl.
 USPC .......................................... 606/148; 606/127
(58) Field of Classification Search
 USPC .............. 606/127, 148, 144, 146, 232
 See application file for complete search history.

(56) References Cited

U.S. PATENT DOCUMENTS

| | | | | |
|---|---|---|---|---|
| 3,791,387 A | * | 2/1974 | Itoh .............................. | 606/113 |
| 5,064,428 A | * | 11/1991 | Cope et al. .................... | 606/127 |
| 5,496,330 A | * | 3/1996 | Bates et al. ................... | 606/127 |
| 5,499,991 A | * | 3/1996 | Garman et al. ............... | 606/148 |
| 5,501,692 A | * | 3/1996 | Riza .............................. | 606/148 |
| 5,643,292 A | * | 7/1997 | Hart ............................. | 606/144 |
| 5,755,728 A | * | 5/1998 | Maki ............................ | 606/145 |
| 5,814,068 A | * | 9/1998 | Koike et al. .................. | 606/228 |
| 5,817,104 A | * | 10/1998 | Bilitz et al. ................... | 606/127 |
| 5,910,148 A | * | 6/1999 | Reimels et al. ............... | 606/144 |
| 5,989,266 A | * | 11/1999 | Foster .......................... | 606/127 |
| 6,022,360 A | * | 2/2000 | Reimels et al. .............. | 606/144 |
| 6,090,129 A | * | 7/2000 | Ouchi .......................... | 606/206 |
| 6,620,166 B1 | | 9/2003 | Wenstrom, Jr. et al. | |
| 6,652,537 B2 | * | 11/2003 | Mercereau et al. ......... | 606/127 |
| 8,523,879 B1 | * | 9/2013 | Lind et al. .................... | 606/127 |
| 2003/0109889 A1 | | 6/2003 | Mercereau et al. | |
| 2004/0097975 A1 | * | 5/2004 | Rose ............................ | 606/145 |

OTHER PUBLICATIONS

German Search Report, Application No. 20 2008 011 769.0, Feb. 17, 2009, 4 pages.

* cited by examiner

*Primary Examiner* — Melanie Tyson
*Assistant Examiner* — Todd J Scherbel
(74) *Attorney, Agent, or Firm* — St. Onge Steward Johnston & Reens LLC

(57) ABSTRACT

A thread catcher for surgical sewing material consisting of a handle, a hollow shaft positioned on the distal side of the handle, and a catching device that is mounted so that it can be slid lengthwise within the hollow shaft by means of a drive element and whose distal end, which can slide out of the distal end of the hollow shaft, is configured as a catcher loop. To create a thread catcher for surgical sewing material that is simple to operate and ensures rapid and secure grasping of the surgical sewing material, it is proposed with the invention that the catcher loop should consist of at least three segments that are distally connected with one another.

5 Claims, 3 Drawing Sheets

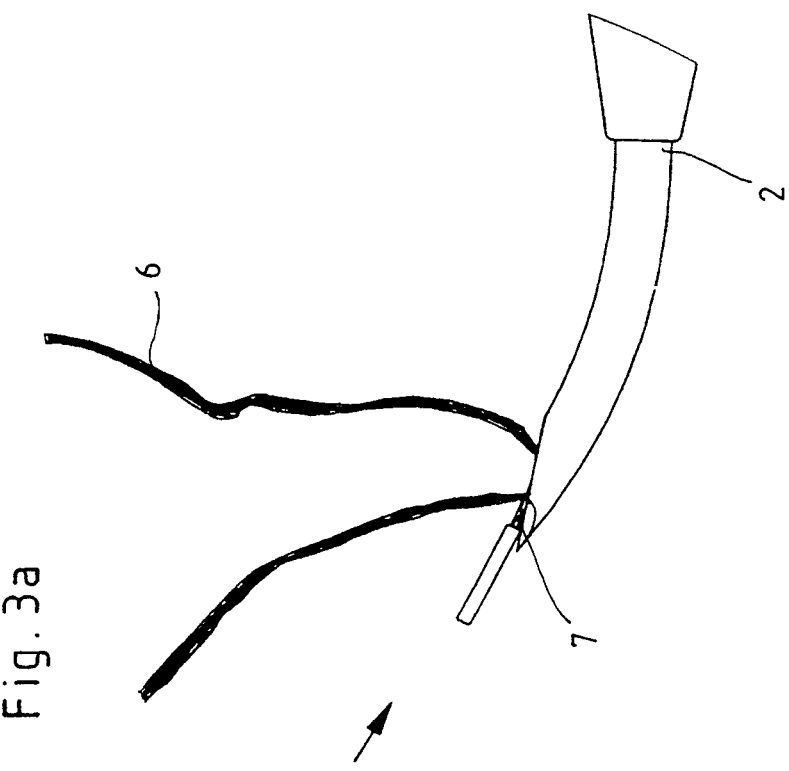
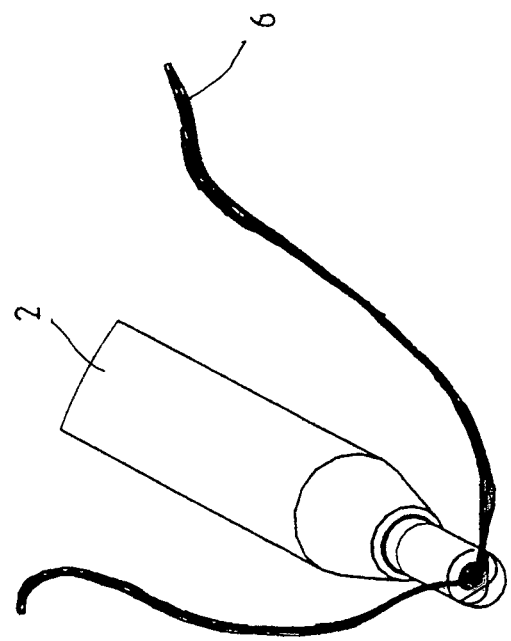
Fig. 3a
Fig. 3b

THREAD CATCHER FOR SURGICAL SEWING MATERIAL

CROSS-REFERENCE TO RELATED APPLICATIONS

The present application claims priority of German patent application No. 20 2008 011 769.0 filed on Sep. 4, 2008, the content of which is incorporated herein by reference.

FIELD OF THE INVENTION

The invention relates to a thread catcher for surgical sewing material, consisting of a handle, a hollows shaft positioned on the distal side of the handle, and a catching device that is mounted so that it can be slid lengthwise within the hollow shaft by means of a drive element and whose distal end, which can be slid out of the distal end of the hollow shaft, is configured as a catcher loop.

BACKGROUND OF THE INVENTION

Surgical thread catchers are used in surgical interventions, in particular in endoscopic procedures, for instance to grip thread ends and pull them through narrow passageway openings.

A generic thread catcher is known in the art, for instance, in U.S. Pat. No. 6,620,166 B1. In this known thread catcher the catcher loop for gripping the thread consists of two wire segments connected to one another on the distal end, which between themselves spread the open catcher loop. In order to grip the thread, the thread catcher must be rotated by the operator in such a way that the thread enters into the catcher loop. Then the catching device is pushed in the proximal direction by the drive element so that the catcher loop closes and fixes the grasped thread.

The disadvantage of thread catchers known in the art is that the thread can be grasped only on one plane and therefore the operator must rotate the thread catcher until said thread catcher is aligned in the correct position with respect to the thread.

It is consequently the object of the invention to create a thread catcher for surgical sewing material that is simple to operate and ensures rapid and secure gripping of the surgical sewing material.

SUMMARY OF THE INVENTION

This object is fulfilled by the invention in that the catcher loop consists of at least three segments connected distally with one another.

As a result of the inventive configuration of the catcher loop as made up of at least three segments, which preferably are positioned with respect to one another in such a way that they encompass more than one plane, it is possible to grasp the thread even without the necessity of rotating the thread catcher, because the at least three segments of the catcher loop encompass other catching planes. This spatial configuration of the catcher loop makes it possible to catch the thread without the necessity of orienting the thread catcher to the thread by rotation.

In order to configure the catcher loop made up of at least three segments in the opened catching position as large as possible, it is proposed with the invention that the segments of the catcher loop should be configured as arched in the position where they are pushed out of the distal end of the hollow shaft.

According to a preferred embodiment of the invention, it is proposed that the segments of the catcher loop should consist of a spring-elastic material. Spring-elastic material has the advantage that the segments, on the one hand, can be drawn together to close the catcher loop without any residual deformation and, on the other hand, they open automatically again to form the catcher loop as soon as the catcher loop emerges from the hollow shaft.

For secure fixing of the grasped thread, it is further proposed with the invention that the catcher loop should be capable of being drawn completely into the hollow shaft by the drive element.

According to a practical embodiment of the invention, the drive element, by which the catching device can be slid within the hollow shaft, is configured as a thrust roller that can be actuated by hand. This configuration of the drive element can be produced in simple and cost-effective manner and in addition has the advantage that the hand actuation, for instance, by means of the thumb, makes it possible for the operator to adjust the sliding of the catching device precisely and sensitively.

Finally, it is proposed with the invention that the hollow shaft should be a hollow sewing needle. This configuration has the advantage that the inventive thread catcher can also be used as a sewing tool.

Additional characteristics and advantages of the invention can be seen by referring to the appended illustrations, in which an embodiment of an inventive thread catcher for surgical sewing material is shown as an example, with restricting the invention to said embodiment.

BRIEF DESCRIPTION OF THE DRAWINGS

FIG. 3a shows a cut-out view of the thread catcher according to FIG. 1 with grasped sewing material, presenting an initial working position.

FIG. 3b shows a view as in FIG. 3a but depicting a subsequent working position.

DETAILED DESCRIPTION OF THE INVENTION

Figure 1:
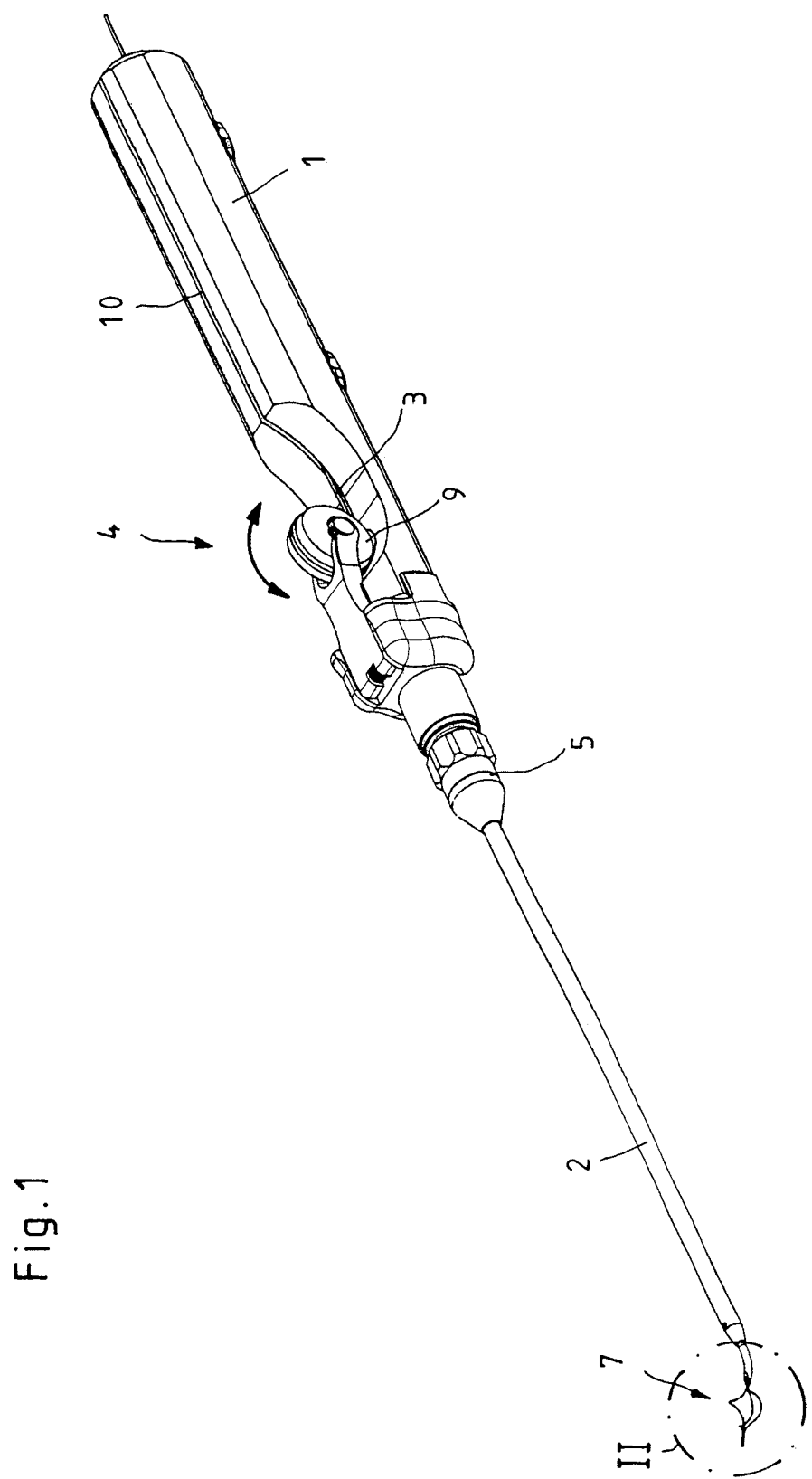
FIG. 1 shows a perspective view of an inventive thread catcher for surgical sewing material.

The thread catcher illustrated in FIG. 1 consists essentially of a handle 1 on the proximal end, a hollow shaft 2 positioned on the distal side of the handle 1, and a catching device 3, which is mounted so that it can be slid longitudinally within the hollow shaft 2 by means of a drive element 4.

In the illustrated embodiment the hollow shaft 2 is configured as a hollow sewing needle, which can be secured on the distal side of the handle 1 by means of a box nut 5.

It is also possible, of course, to connect the hollow shaft 2 with the handle 1 by means of a catching or plug-in connection of the like. It is essential that the catching device 3 can be slid longitudinally inside the hollow shaft 2 by means of the drive element 4 positioned on the handle 1.

Figure 2:
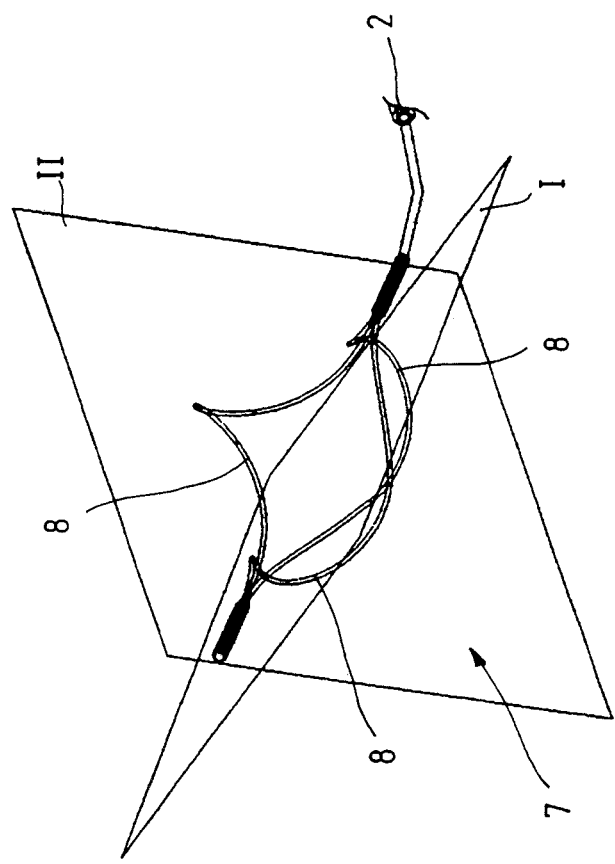
FIG. 2 shows an enlarged view of detail 11 from FIG. 1.

For grasping and holding a thread 6, the distal end of the catching device 3 that is mounted so that it can be slid within the hollow shaft 2 is configured as a catcher loop 7, which, as can be seen in particular from the detail view of FIG. 2, consists in the illustrated embodiment of three segments 8, which are connected distally with one another.

The three segments 8 of the catcher loop 7 are positioned with respect to one another in such a way that they span two planes I and II that are positioned essentially perpendicularly to one another and thus facilitate the threading of the thread 6 into the catcher loop 7 without the necessity of adjusting the thread catcher with respect to the thread 6 by rotation.

In addition to the illustrated embodiment with three segments 8, it is also possible, of course, to construct the catcher loop 7 with more than three segments 8.

As can also be seen from FIG. 2, the segments 8 of the catcher loop 7 are configured as arched in the position extending from the hollow shaft 2 on the distal end, in order to form the greatest possible opening of the catching loop 7.

The segments 8 of the catcher loop 7 consist preferably of a spring-elastic material. Spring-elastic material has the advantage that the segments 8, on the one hand, can be compressed back together to close the catcher loop 7 without any residual deformation and, on the other hand, automatically open again to form the catcher loop 7 as soon as the catcher loop 7 emerges out of the hollow shaft 2.

Sliding of the catching device 3 occurs by means of the drive element 4 that is positioned on the handle 1 and which in the illustrated embodiment is configured as a hand-actuated thrust roller 9.

The thread catcher, described above, is actuated as follows:

To start, the hollow shaft 2 configured as a hollow sewing needle is secured on the handle by means of the box nut 5 and then the catching device 3 is inserted into the handle 1 by way of a groove 10, which is configured in the handle 1 and is open at the top, and then is slid in the distal direction until the catching device 3 enters into the hollow shaft 2.

To pick up a thread 6, the operator slides the catching device 3 in the distal direction by means of the drive element 4 until the catcher loop 7 configured on the distal end of the catching device 3 emerges out of the distal end of the hollow shaft 2 and the spring-elastic segments 8 form the spatial catcher loop 7 illustrated in FIGS. 1 and 2.

Actuation of the drive element 4, configured as a thrust roller 9, is accomplished by the operator, for instance with the thumb, rotating the thrust roller 9 in the proximal direction in order to slide the catching device in the distal direction out of the hollow shaft 2 and, in reverse, rotating the thrust roller 9 in the distal direction in order to slide the catching device 3 in the proximal direction into the hollow shaft 2.

As soon as the thread 6 that is to be grasped has entered into the catcher loop 7 that has been expanded spatially into two planes, the operator pulls the catching device 3 in the proximal direction by means of the drive element 4 until the catcher loop 7 enters into the distal end of the hollow shaft 2 and the thread 6 is drawn together so that it is fixed, as shown in FIGS. 3a and 3b.

A thread catcher configured in this manner is distinguished in that the thread 6 that is to be grasped can be caught because of the spatial configuration of the catcher loop 7 without requiring the operator to align the thread catcher with the thread 6 by rotating the entire thread catcher.

The invention claimed is:

1. A thread catcher for surgical sewing material comprising a handle, a hollow shaft positioned on a distal side of the handle, and a catching device that is mounted so that it can be slid lengthwise within the hollow shaft by means of a drive element and whose distal end, which can slide out of a distal end of the hollow shaft, is configured as a catcher loop, which has at least three segments that are proximally connected to the distal end of the catching device and that are distally connected with one another, wherein the at least three segments are positioned with respect to one another to encompass more than one plane so that the catcher loop makes it possible to catch the thread without orienting the thread catcher to the thread by rotation and wherein the catcher loop is drawn completely into the hollow shaft in a grasping position for fixing a grasped thread between the at least three segments;

wherein a groove running from a proximal end of the handle in a lengthwise direction of the handle and which is open to a top is configured in the handle for inserting the catching device;

wherein the drive element slides the catching device in the lengthwise direction relative to the handle.

2. The thread catcher according to claim 1, wherein the segments of the catcher loop are configured as arched in the position where they are pushed out of the distal end of the hollow shaft.

3. The thread catcher according to claim 1, wherein the segments of the catcher loop consist of a spring-elastic material.

4. The thread catcher according to claim 1, wherein the drive element is configured as a hand-actuated thrust roller.

5. The thread catcher according to claim 1, wherein the hollow shaft is a hollow sewing needle.

* * * * *